United States Patent
Tsukada (12) 
(10) Patent No.: US 6,302,850 B1
(45) Date of Patent: Oct. 16, 2001

(54) FUNDUS BLOOD FLOW METERING METHOD

(75) Inventor: Mamoru Tsukada, Fujisawa (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 09/392,304

(22) Filed: Sep. 8, 1999

(30) Foreign Application Priority Data

Sep. 10, 1998 (JP) .................................................. 10-274347

(51) Int. Cl.[7] ...................................................... A61B 5/02
(52) U.S. Cl. ........................... 600/504; 600/479; 600/318
(58) Field of Search ............................ 600/504, 407, 600/318, 479, 480; 351/206, 208, 211, 215, 216; 356/27, 28, 39–47

(56) References Cited

U.S. PATENT DOCUMENTS 5,129,400 * 7/1992 Makino et al. ....................... 600/479
5,640,963 * 6/1997 Tanaka ................................. 600/470

* cited by examiner

*Primary Examiner*—Eric F. Winakur
(74) *Attorney, Agent, or Firm*—Fitzpatrick, Cella, Harper & Scinto (57) ABSTRACT

A fundus blood flow metering method includes a series of steps of carrying out alignment of the positional relation with an eye to be examined, carrying out aiming of a blood vessel to be measured, and measuring a velocity of blood flow while tracking the blood vessel so as to track and capture eye movement. After the sequential operation, the direction of incidence of a measuring beam is switched to another direction and the series of steps are again carried out for the same blood vessel, starting from the alignment.

11 Claims, 8 Drawing Sheets

FUNDUS BLOOD FLOW METERING METHOD

BACKGROUND OF THE INVENTION

1. Field of the Invention

The present invention relates to a fundus blood flow metering method for examining a blood flow state at the fundus of an eye based on the laser Doppler method.

2. Related Background Art

Figure 9:
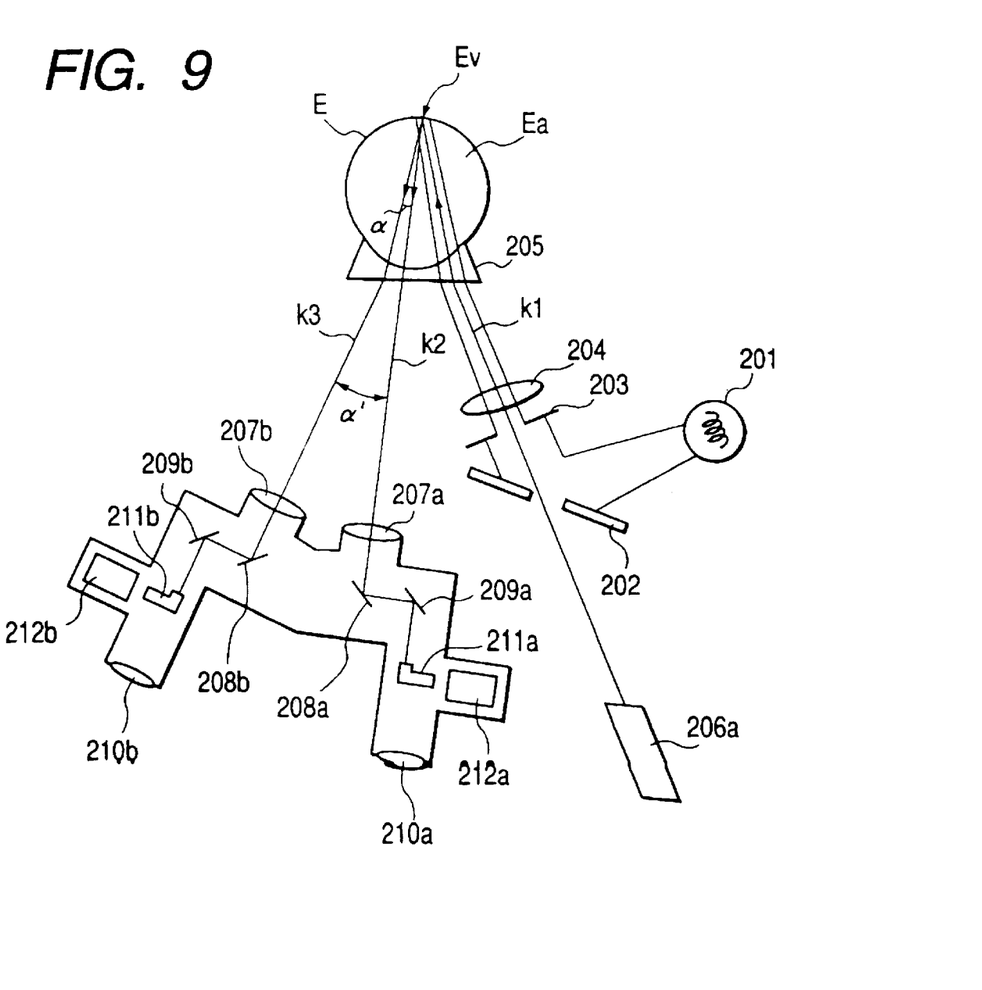
FIG. 9 is a structural diagram of the conventional example.

FIG. 9 is a structural diagram of a conventional fundus-blood-flow meter, which is a modification of the slit lamp commonly used for ophthalmic examination. An illumination optical system is placed on an optical path K1 and white light from an illumination-light source 201 is reflected by a perforated mirror 202 to illuminate a blood vessel Ev on the fundus oculi Ea through a contact lens 205 for canceling the refracting power of the cornea of the eye E to be examined, so as to permit observation of the fundus Ea. A measurement-laser-light source 206 for emitting He—Ne laser light is placed on an optical path behind the perforated mirror 202 and measuring light from the measurement-laser-light source 206 passes through the aperture in the center of the perforated mirror 202 to be coaxially aligned with the beam from the illumination light source 201 and irradiate the fundus Ea in a spot shape.

Light scattered and reflected by blood cells flowing in the blood vessel Ev, and by the vessel wall travels through objective lenses 207a, 207b of a light-receiving optical system for stereoscopic observation, which are placed on respective optical paths K2, K3 making an angle α', and each beam is then reflected by a mirror 208a, 208b and a mirror 209a, 209b to pass through eyepiece 210a, 210b. The light through the eyepieces 210a, 210b is observed as a fundus image by an examiner, and the examiner selects a measured part while observing the fundus Ea through the eyepieces 210a, 210b.

Figure 10:
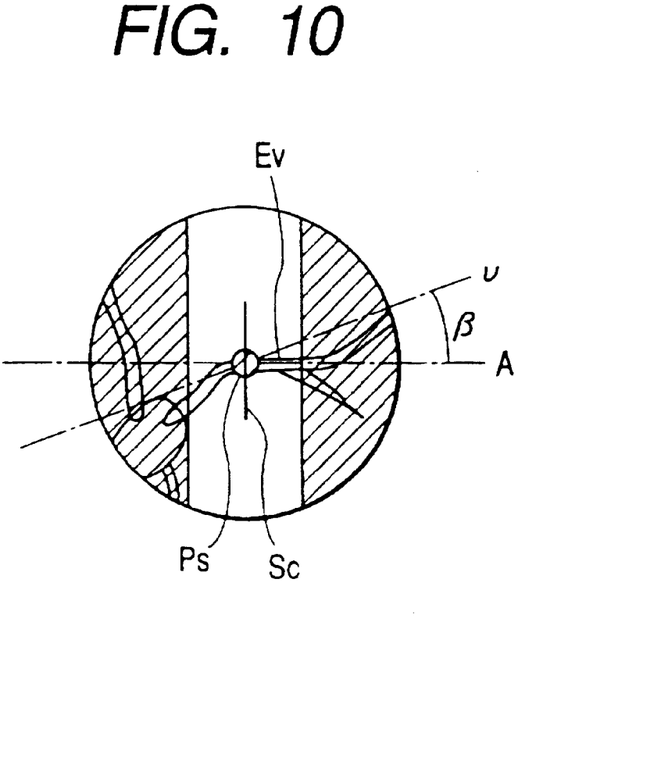
FIG. 10 is an explanatory diagram of a fundus image.

FIG. 10 shows a fundus image to be observed by the examiner. When the blood vessel Ev (to be a measured object) is aligned with a scale SC preliminarily prepared on the focal plane of the eyepieces 210a, 210b within the area illuminated by the illumination light, the axis of the measuring light from the measurement-laser-light source 206 is aligned with the blood vessel Ev, so that the measured part is determined by the spot beam PS from the measurement-laser-light source 206, At this time, reflected light of the measuring light from the fundus Ea is received via optical fibers 211a, 211b by photomultipliers 212a, 212b.

This received signal includes a predetermined beat-signal component resulting from interference between a component undergoing a Doppler shift by the blood flow flowing into the blood vessel Ev and a component reflected by the vessel wall at a standstill, and the velocity of blood flow in the blood vessel Ev is obtained by frequency analysis of this beat signal.

Figure 11:
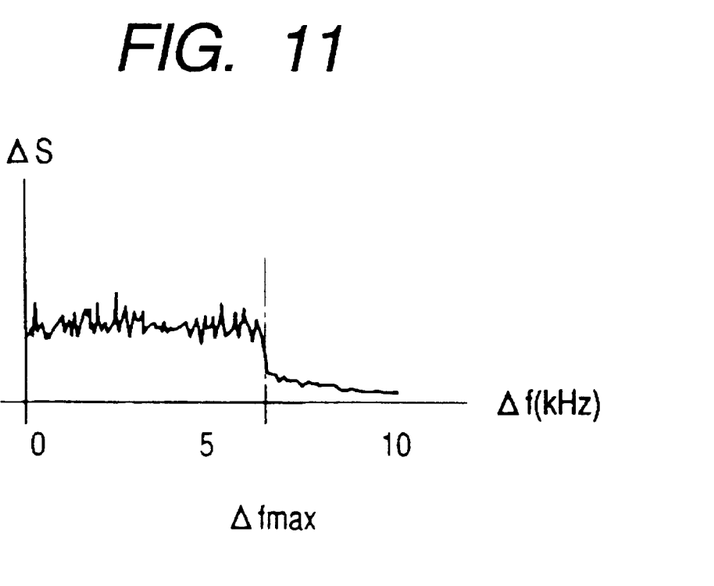
FIG. 11 is a graph of the frequency distribution of received signal.

FIG. 11 shows an example of the result of the frequency analysis of received signals measured by the photomultipliers 212a, 212b, in which the axis of the abscissas represent the frequency Δf and the axis of the ordinates represent the output AS thereof. The relationship among the maximum shift Δfmax of frequency, the wave vector κi of the incident light, the wave vector κS of the received light, and the velocity vector v of the blood flow can be expressed by the following equation.

$$\Delta fmax = (\kappa s - \kappa i) \cdot v \quad (1)$$

Therefore, the maximum velocity of the blood flow Vmax can be expressed by the below equation by modifying Eq. (1), using the maximum frequency shifts Δfmax1, Δfmax2 computed from the respective received signals by the photomultipliers 212a, 212b, the wavelength λ of the laser light, the refractive index n of the measured part, the angle a between the optical axes of the received light beams K2, K3 in the eye, and the angle β between the velocity vector v of the blood flow and a plane made by the reception optical axes K2, K3 in the eye.

$$Vmax = \{\lambda/(n \cdot \alpha) \cdot |\Delta fmax1 - \Delta fmax2|\}/\cos \beta \quad (2)$$

By carrying out the measurement from two directions in this way, the contribution of the direction of incidence of the measuring light is canceled, so that the velocity of blood flow can be measured at an arbitrary part on the fundus Ea.

For measuring the true blood-flow velocity from the relationship between the intersecting line A between the plane made by the two reception optical paths K2, K3 and the fundus Ea, and the angle P between this intersecting line A and the blood-flow-velocity vector, the intersecting line A needs to be aligned with the velocity vector to satisfy β=0° in Eq. (2). For this reason, an image rotator is placed in the reception optical system to align them with each other on an optical basis.

In practical measurement, it is, however, necessary to check signs of Δfmax1 and Δfmax2 computed in this state of β=O. A measurement time necessary for computation of an average flow velocity of an artery blood flow at the fundus Ea is not less than a period of one pulsation in each measurement, which is approximately two seconds for safety. In order to carry out the measurement during this period, the measuring beam must irradiate the measured vessel correctly. For this reason, recent fundus blood flow meters are provided with a tracking means for tracking and capturing the measured part according to eye movement.

In the above conventional example, however, for continuously carrying out the measurement with switching the angle of incidence of the measuring beam to the eyeball, the measurement has to be carried out continuously for the period of time of about four seconds. During execution of this continuous measurement for four seconds, however, there are cases wherein the contrast of the fundus image is temporarily lowered because of nictation, a tear, oil film of the eye, fixation failure of the patient, and so on, so as to lose blood-vessel position information from the fundus video signals during that period, thus making the tracking operation unstable. There is also another problem that the load is great on the patient and the restraint time of the eye of the patient becomes long.

Further, in order to carry out accurate measurement, it is necessary to correct the positional deviation between the measuring beam and the measured blood vessel due to aberration of the eye E to be examined and to set the measurement conditions including adjustment of sensitivity of the photoreceptors for every switching of the angle of incidence of the measuring beam. Therefore, if the measurement is intended to be carried out continuously, the state of the eye E to be examined will be much worse the longer measurement takes. Particularly, in cases wherein the examiner himself or herself needs to adjust the system to effect the correction for the positional deviation between the measuring beam and the measured blood vessel or the like, there will arise such issues as incorrect operation and failure in correct adjustment because of inaccuracy of adjustment procedures.

SUMMARY OF THE INVENTION

An object of the present invention is to provide a fundus-blood-flow metering method overcoming the above problens that can obtain the velocity of blood flow accurately while decreasing the load on the patient, by carrying out the optimum adjustment in every measurement.

The present invention provides a fundus-blood-flow metering method for metering a blood flow with irradiation means for irradiating a measured part of a blood vessel at fundus oculi with a measuring beam from first and second irradiation directions, light receiving means for receiving scattered and reflected light from the measured part in two directions, and computing means for computing the velocity of the blood flow, based on an output signal from the light receiving means, the method comprising a first measurement step of measuring the blood flow from the first irradiation direction, a second measurement step of measuring the blood flow from the second irradiation direction different from the first irradiation direction in the first measurement step, and an alignment step of carrying out alignment of the positional relation with an eye to be examined, during execution of each of said first and second measurement steps.

The fundus-blood-flow metering method further comprises a gain control step of controlling the gain of the light receiving means, prior to measurement with the light receiving means, when executing the first and second measurement steps.

DETAILED DESCRIPTION OF THE PREFERRED EMBODIMENTS

The present invention will be described in detail based on the embodiments illustrated in FIG. 1 to FIG. 8.

Figure 1:
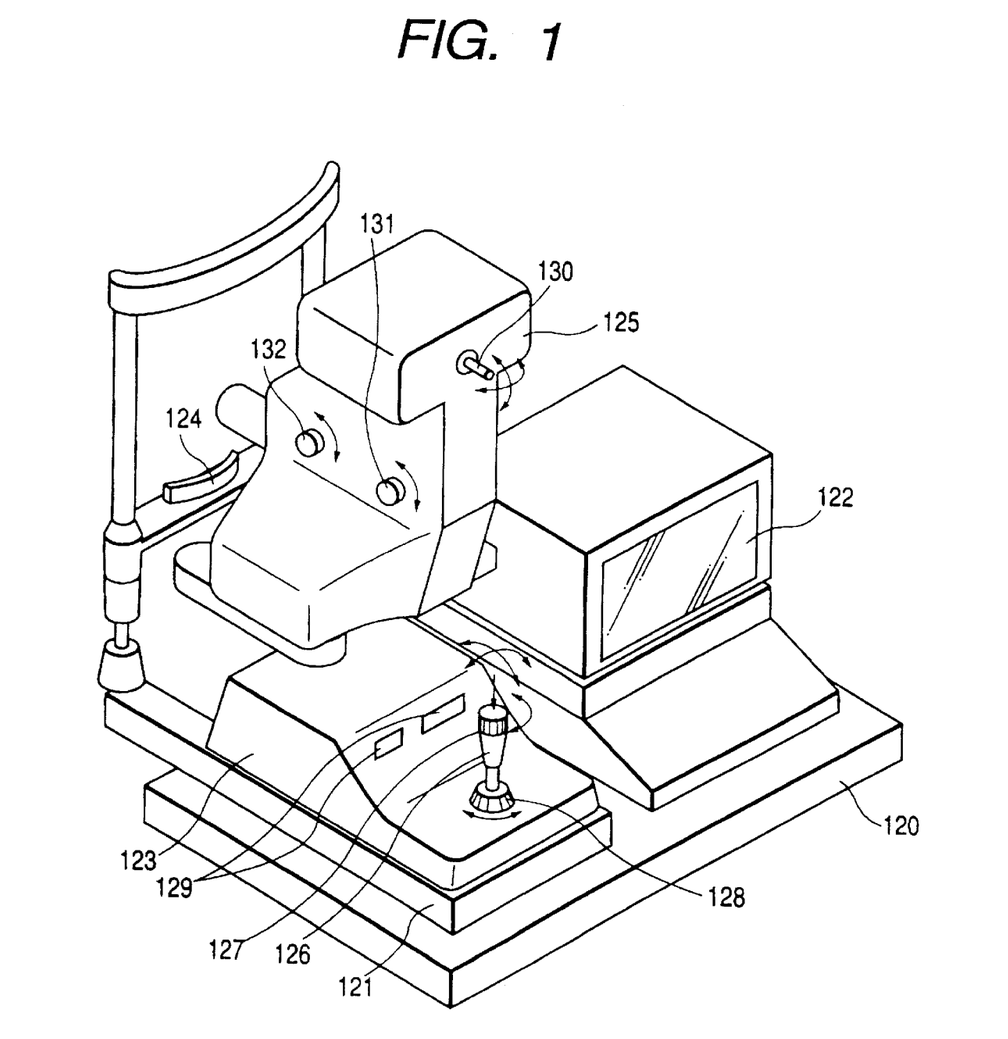
FIG. 1 is a perspective view of an apparatus of an embodiment.

FIG. 1 is a perspective view of a fundus blood flowmeter of an embodiment, in which a stage securing part 121 and a personal computer 122 are mounted on a table 120 and in which a stage movable portion 123 and a jaw support 124, movable back and forth and left and right, are secured to the stage securing part 121. A main-body measurement head 125 is mounted on the stage movable portion 123, and provided on the examiner side thereof are a control rod 126, a measurement switch 127, a tracking adjustment dial 128, and LEDs 129 for display. The main-body measurement head 125 is provided with an internal fixation light control knob 130, a focus knob 131, and an image rotator knob 132.

Figure 7:
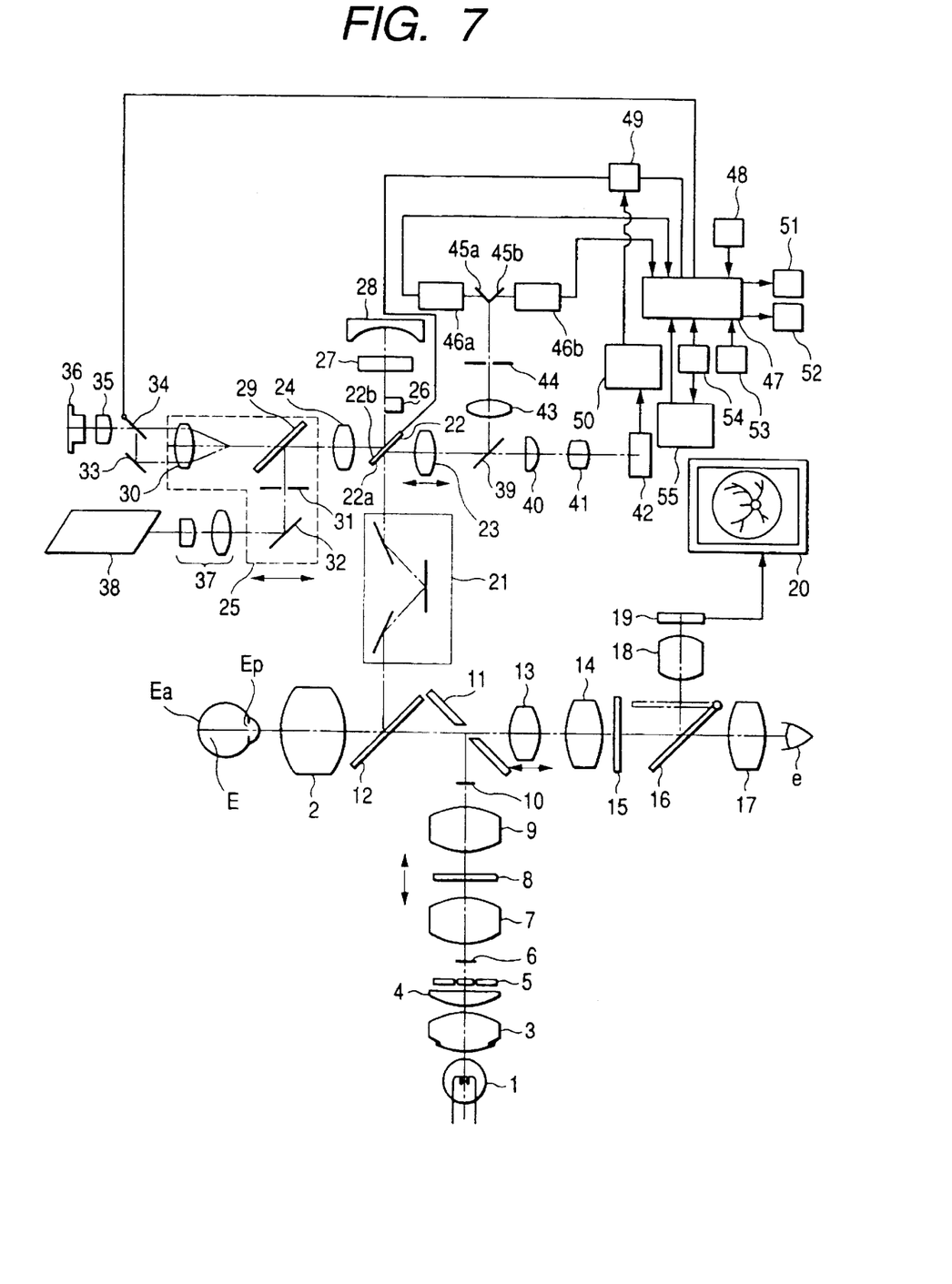
FIG. 7 is a block diagram to show an apparatus according to the present invention.

FIG. 7 is a structural diagram of an embodiment of application to the fundus blood flowmeter. On an illumination optical path from an observation light source 1 comprised of a tungsten lamp to emit white light, or the like to an objective lens 2 opposed to the eye E to be examined, an illumination optical system is constructed by successively arranging a condenser lens 3, a field lens 4 provided with a bandpass filter for transmitting, for example, only light of wavelengths in the yellow region, a ring slit 5 located at a position approximately conjugate with the pupil Ep of the eye E to be examined, a shield member 6 located at a position approximately conjugate with the crystalline lens of the eye E to be examined, a relay lens 7, a transmissive liquid-crystal panel 8 as a fixation-target displaying element movable along the optical path, a relay lens 9, a shield member 10 disposed conjugate with the proximity of the cornea of the eye E to be examined, a perforated mirror 11, and a band-pass mirror 12 for transmitting the light of wavelengths in the yellow region but reflecting other light.

A fundus-observation optical system is constructed behind the perforated mirror 11 by successively arranging a focusing lens 13 movable along the optical path, a relay lens 14, a scale plate 15, an optical-path switching mirror 16 capable of being put in or out of the optical path, and an eyepiece 17, then reaching the eye of the examiner. A TV relay lens 18 and a CCD camera 19 are disposed on an optical path along the reflection direction of the optical-path switching mirror 16 put in the optical path, and the output of the CCD camera 19 is connected to a liquid-crystal monitor 20.

An image rotator 21 and a galvanometric mirror 22, which has a rotation axis normal to the plane of the drawing and which the both surfaces polished, are positioned on an optical path along the reflection direction of the band-pass mirror 12. A focus lens 23 movable along the optical path is disposed in the reflection direction of a lower reflecting surface 22a of the galvanometric mirror 22. A lens 24 and a focus unit 25, movable along the optical path, are located in the reflection direction of an upper reflecting surface 22b of the galvanometric mirror 22. The front focal plane of the lens 24 is conjugate with the pupil Ep of the eye E to be examined and the galvanometric mirror 22 is positioned on that focal plane.

Above the galvanometric mirror 22 in the drawing, a relay optical system is constructed by successively arranging an optical-pathlength-compensating semicircular plate 26, a black spot plate 27 having a shield portion in the optical path, and a concave mirror 28 and is arranged so that a beam not reflected but transmitted by the lower reflecting surface 22a of the galvanometric mirror 22 is guided back to the upper reflecting surface 22b of the galvanometric mirror 22. The optical-path-length-compensating semicircular plate 26 acts to correct deviation in the vertical direction in the drawing, of the positions of the upper reflecting surface 22b and the lower reflecting surface 22a of the galvanometric mirror 22 because of the thickness of the mirror, and acts only in the optical path extending to the image rotator 21.

In the focus unit 25, a dichroic mirror 29 and a condenser lens 30 are arranged in order on the same optical path as the lens 24, and a mask 31 and a mirror 32 are arranged on an optical path along the reflection direction of the dichromic mirror 29. This focus unit 25 is arranged so as to be integrally movable in the directions indicated by arrows.

A fixed mirror 33 and an optical-path switching mirror 34 retractable from the optical path are arranged in parallel on the optical path on the incidence side of the lens 30, and a collimator lens 35 and a laser diode 36 for measurement, which emits, for example, coherent red light, are arranged on the optical path on the incidence side of the optical path switching mirror 34. Further, a beam expander 37 comprised of cylindrical lenses or the like, and a tracking light source 38, which emits, for example, green light of high luminance different from the other light sources, are arranged on an optical path on the incidence side of the mirror 32.

On the optical path along the reflection direction of the lower reflecting surface 22a of the galvanometric mirror 22, a blood-vessel detecting system is composed by successively arranging the focusing lens 23, a dichroic mirror 39, a field lens 40, a magnifying lens 41, and a one-dimensional CCD 42 provided with an image intensifier. An imaging lens 43, a confocal stop 44, and a pair of mirrors 45a, 45b approximately conjugate with the pupil Ep of the eye E to be examined are disposed on an optical path along the reflection direction of the dichroic mirror 39 and photomultipliers 46a, 46b are located in respective reflection directions of the mirror pair 45a, 45b, thus composing a light-receiving optical system for measurement. Although all the optical paths are illustrated on the same plane for the convenience of illustration, the reflection optical paths of the mirror pair 45a, 45b, the measurement optical path in the emission direction of the tracking light source 38, and the optical path from the laser diode 36 to the mask 31 are perpendicular to the plane of the drawing.

Further, the apparatus is provided with a system control unit 47 for controlling the entire apparatus, and connected to this system control unit 47 are an input device 48, which the examiner manipulates, and the outputs of the photomultipliers 46a, 46b. Outputs of the system control unit 47 are connected respectively to a galvanometric-mirror control circuit 49 for controlling the galvanometric mirror 22 and to the optical-path switching mirror 34. An output of the one-dimensional CCD 42 is connected via a blood-vessel-position detecting circuit 50 to the galvanometric-mirror control circuit 49, outputs of the system control unit 47 are connected respectively to a measurement-result display device 51, to a measurement-data selecting device 52, to an optical-path switching input device 53, and to a memory 54, an output of the memory 54 is connected to an arithmetic-operation unit 55, and an output of the operation unit 55 is connected to the system control unit 47.

Figure 8:
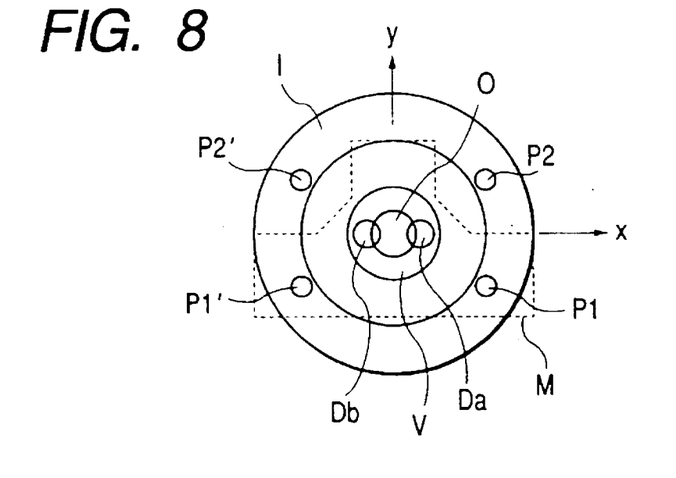
FIG. 8 is a diagram for explaining arrangement of beams on the pupil.

FIG. 8 shows the arrangement of beams on the pupil Ep of the eye E to be examined, in which I represents an image of the ring slit 5 as an area illuminated by the yellow illumination light, O denotes an image of the aperture of the perforated mirror 11 as a fundus observation beam, V denotes an image of the effective area of the upper and lower reflecting surfaces 22b, 22a of the galvanometric mirror 22 as a measuring/blood vessel reception light beam, and Da, Db denote images of the respective mirrors 45a, 45b as two measuring reception beams. P2, P2' are the positions of incidence of the measuring light, which are positions of the measuring light selected by switching of the optical-path switching mirror 34, and an area M, indicated by a dashed line, represents an image of the lower reflecting surface 22a of the galvanometric mirror 22.

During measurement, the white light emitted from the observation light source 1 travels through the condenser lens 3 to enter the field lens 4 provided with the band-pass filter. It transmits only light of wavelengths in the yellow region and the yellow light travels via the ring slit 5, the shield member 6, and the relay lens 7 to illuminate the transmissive liquid-crystal panel 8 from the back. Further, this beam travels via the relay lens 9 and the shield member 10 to be reflected by the perforated mirror 11. Only the light of wavelengths in the yellow region is transmitted by the band-pass mirror 12 and then travels through the objective lens 2 to be focoused once as a fundus-illumination-beam I on the pupil Ep of the eye E to be examined. After that, the yellow light illuminates the fundus Ea almost uniformily.

At this time, the transmissive liquid-crystal panel 8 displays a fixation target, which is projected onto the fundus Ea of the eye E to be examined, by the illumination light to be presented as a target image to the eye E to be examined. The ring slit 5 and the shield members 6, 10 are provided for separating the fundus illumination light from the fundus observation light at the anterior part of the eye E to be examined, and the shape thereof can be arbitrary as long as they can form the necessary shield area.

Reflected light from the fundus Ea is extracted as a fundus observation beam O from on the pupil Ep to return through the same optical path, and it then travels through the aperture in the center of the perforated mirror 11, the focusing lens 13, and the relay lens 14 to be focused as a fundus image Ea' on the scale plate 15. Then the light reaches the optical path switching mirror 16. When the optical path switching mirror 16 is retracted from the optical path, the examiner's eye e can observe the fundus image Ea' through the eyepiece 17. When the optical path switching mirror 16 is inserted in the optical path on the other hand, the fundus image Ea' focused on the scale plate 15 is refocused on the CCD camera 19 by the TV relay lens 18 to be displayed on the liquid-crystal monitor 20.

The examiner carries out alignment of the apparatus while observing this fundus image Ea' through the eyepiece 17 or through the liquid-crystal monitor 20. At this time, it is preferable to employ a suitable observation method according to a purpose. Since the observation through the eyepiece 17 normally presents higher resolution and higher sensitivity than that through the liquid-crystal monitor 20 or the like, it is suitable for diagnosis based on reading of a minute change of the fundus Ea. On the other hand, the observation through the liquid-crystal monitor 20 imposes less fatigue on the examiner, because there is nothing limiting the field. Further, when the output of the CCD camera 19 is connected to an external video tape recorder or video printer or the like, a change of the measured part on the fundus EA can be electronically recorded sequentially, which is extremely effective from the clinical point of view.

Next, the measuring light emitted from the laser diode 36 is collimated by the collimator lens 35. When the optical-path switching mirror 34 is put in the optical path, the measuring light is reflected by the optical-path switching mirror 34 and the fixed mirror 33 to pass the lower part of the condenser lens 30. When the optical-path switching mirror 34 is retracted from the optical path, the measuring light travels directly through the upper part of the condenser lens 30 to be transmitted by the dichroic mirror 29.

On the other hand, the tracking light emitted from the tracking light source 38 is expanded the beam diameter at different vertical and lateral magnifications by the beam expander 37 and is then reflected by the mirror 32. After that, the tracking light is shaped in a desired shape by the shaping mask 31 and is reflected by the dichroic mirror 29. Then the tracking light is superimposed on the measuring light focused in a spot shape at the position conjugate with the center of the aperture of the mask 31 by the condenser lens 30.

The measuring light and the tracking light thus superimposed travels through the lens 24 to be once reflected by the upper reflecting surface 22b of the galvanometric mirror 22. Then the measuring light and the tracking light travels through the black spot-plate 27 to be reflected by the concave mirror 28. The measuring light and tracking light travels again through the black-spot plate 27 and the optical-pathlength-compensating semicircular plate 26 back to the galvanometric mirror 22. Since the galvanometric mirror 22 is located at the position conjugate with the pupil Ep of the eye E to be examined, the image thereof has the shape indicated by the dashed line M of FIG. 8 on the pupil Ep of the eye E to be examined.

Since the concave mirror 28, the black-spot plate 27, and the optical-pathlength-compensating semicircular plate 26 are coaxially arranged on the optical path and are provided with the function of the relay optical system for focusing the upper reflecting surface 22b and the lower reflecting surface 22a of the galvanometric mirror 22 at a magnification of −1, the beams reflected at the positions P1, P1' of FIG. 8 on the back side of the image M of the galvanometric mirror 22 by insertion into and retraction out of the optical path of the optical path switching mirror 34 are guided back to the positions of P2, P2', respectively, located in the cut portions of the galvanometric mirror 22 and thus travel toward the image rotator 21 without being reflected by the galvanometric mirror 22. Then, the beams passing through the image rotator 21 are deflected toward the objective lens 2 by the band-pass mirror 12 to be projected through the objective lens 2 onto the fundus Ea of the eye E to be examined.

Since the measuring light and the tracking light are incident on the galvanometric mirror 22 in a decentered state from the optical axis of the objective lens 2 when reflected in the upper reflecting surface 22b of the galvanometric mirror 22 and returned thereto, as described above, the measuring light and tracking light irradiate the fundus Ea in a dot shape after focused as a spot image P2 or P2' on the pupil Ep as illustrated in FIG. 8.

Scattered and reflected light at the fundus Ea is again condensed by the objective lens 2 to be reflected by the band-pass mirror 12. Then, the light travels through the image rotator 21 to be reflected by the lower reflecting surface 22a of the galvanometric mirror 22. Then, the light travels through the focusing lens 23 and the dichroic mirror 39 separates the measuring light from the tracking light.

The tracking light is transmitted by the dichroic mirror 39 and is focused as a larger blood-vessel image than the fundus image Ea' formed by the fundus observation optical system, on the one-dimensional CCD 42 by the field lens 40 and the imaging lens 41. Then, based on a blood-vessel image Ev' picked up by the one-dimensional CCD 42, the blood-vessel position detecting circuit 50 prepares data indicating a moving amount of the blood-vessel image Ev' and outputs the data to the galvanometric mirror control circuit 49. The galvanometric-mirror control circuit 49 actuates the galvanometric mirror 22 so as to compensate for this moving amount.

On the other hand, the measuring light is reflected by the dichroic mirror 39 and travels through the lens 43 and the aperture of the confocal stop 44. Then, the measuring light is reflected by the mirror pair 45a, 45b to be received by the respective photomultipliers 46a, 46b. Each of the outputs from the photomultipliers 46a, 46b is outputted to the system control unit 47, and this received signal is subjected to the frequency analysis similar to that in the prior art example to calculate the velocity of blood flow at the fundus Ea.

At this time, the illumination light from the observation light source 1 does not reach the one dimensional CCD 42 because of the spectral characteristics of the band-pass mirror 12. Further, malignant flare light is also unlikely to be mixed, because the image pickup range is set to a narrow band. Therefore, only the blood-vessel image Ev' by the tracking light is formed on the one-dimensional CCD 42. Since the spectral reflectances are largely different in the green wavelength region between hemoglobin in the blood and melanin on the pigment epithelium, the blood-vessel image Ev' can be picked up with good contrast by using the green light as the tracking light.

Part of the scattered and reflected light at the fundus Ea from the measuring light and the tracking light is transmitted by the band-pass mirror 12 to be guided to the fundus-observation optical system behind the perforated mirror 11. The tracking light is focused as a bar-shaped indicator on the scale plate 15, while the measuring light is focused as a spot image in the central part of this indicator. These images are observed together with the fundus image Ea' and the target image through the eyepiece 17 or through the liquid-crystal monitor 20. At this time, the spot image (not illustrated) is observed as superimposed at the center of the indicator, and the indicator can be moved one-dimensionally on the fundus Ea by the control member, such as the control rod (126 in FIG. 1) or the like of the input device 48.

The examiner first carries out focusing of the fundus image Ea'. When the examiner adjusts the focus knob 131 of FIG. 1, the transmissive liquid-crystal panel 8, focusing lenses 13, 23, and focus unit 25 are moved in conjunction along the optical path by driving means (not illustrated). When the fundus image Ea' is in focus, the transmissive liquid-crystal panel 8, the scale plate 15, the one-dimensional CCD 42, and the confocal stop 44 become conjugate with the fundus Ea simultaneously.

After completion of the focusing, the indicator is rotated by manipulating the image rotator 21 (132 of FIG. 1) by the control rod 126 of FIG. 1 so that the indicator becomes normal to the running direction of the blood vessel Ev as a measured object.

At this time, since the fundus observation light does not pass through the image rotator 21, the examiner perceives as if only the indicator rotates. Therefore, the image of each optical member on the pupil Ep, illustrated in FIG. 8, is also rotated in the same direction and by the same angle about the center at the origin, so that the straight line connecting the centers of the measurement reception beams Da, Db and the straight line connecting the centers of the spot images P, P', i.e., the x-axis, become aligned with the running direction of the blood vessel Ev.

This operation is equivalent to making $\beta=0°$ in Eq. (2) for computation of velocity described in the prior art example, and this accomplishment of $=0°$ provides the following advantages (a) to (c).

(a) It is seen from Eq. (2) that when $\beta=90°$ or $\cos \beta=0$, the absolute value of the maximum blood-flow velocity Vmax cannot be obtained from the maximum frequency shifts $\Delta f_{max1}$ and $f_{max2}$. This unmeasurable position can be avoided by rotating the fundus image E' so as to achieve $\beta=0°$.

(b) Since the angle $\beta$ does not have to be measured, error factors are reduced and the operation is simplified.

(c) Since the velocity of blood flow is calculated from the interference signal between the scattered and reflected light from the blood-vessel wall and the scattered and reflected light in the blood as described in the prior art example, the measurement result is unchanged even with motion of the fundus Ea in the x-axis direction during the measurement as long as the blood vessel Ev is approximately parallel to the x-axis direction.

On the other hand, when the fundus Ea moves in the y-axis direction perpendicular to the x-axis, the light from the laser diode 36 for measurement deviates from the blood vessel Ev at the measured part to make measured values unstable. In that case, the moving amount of the blood vessel Ev needs to be detected only in the y-axis direction. In the present embodiment, the tracking is carried out only in this single direction by the blood-vessel detecting system behind the dichroic mirror 39, and the galvanometric mirror 22.

In order to measure blood-vessel velocities accurately and quickly as to all blood vessels Ev to be examined with carrying out this tracking, the one-dimensional CCD 42 for detecting the moving amount of the blood vessel image Ev' is to be placed normally to the blood vessel Ev as a measured object. Further, the setting of $\beta=0°$ also presents an advantage of obviating the need for use of the two-dimensional sensor.

In the present embodiment, elements of the one-dimensional CCD 42 are arrayed along the longitudinal direction of the tracking light and, after completion of the angle adjustment of the measured part, the longitudinal direction of the indicator to indicate the tracking light is perpendicular to the running direction of the measured blood vessel Ev. The enlarged fundus image Ea' indicated by the indicator is formed on the one-dimensional CCD 42 of the blood-vessel detecting system.

After completion of the angle adjustment, the examiner controls the control rod of the input device 48 to select a measured part by aligning the spot image superimposed on the tracking light with the measured part. After determining the measured part, the examiner again manipulates the input device 48 to input a command of tracking start.

When the command of tracking start is supplied from the input device 48 through the system control unit 47 to the galvanometric-mirror control circuit 49, the blood-vessel-position detecting circuit 50 computes the moving amount of the blood-vessel image Ev' from a one-dimensional reference position, based on received light signals of the one-dimensional CCD 42. Then, the galvanometric-mirror control circuit 49 actuates the galvanometric mirror 22 according to the moving amount to control it so as to keep the received image position of the blood vessel image Ev' constant on the one-dimensional CCD 42.

After confirming the tracking start, the examiner depresses the measurement switch, not illustrated, of the input device 48 to start the measurement.

Figure 2:
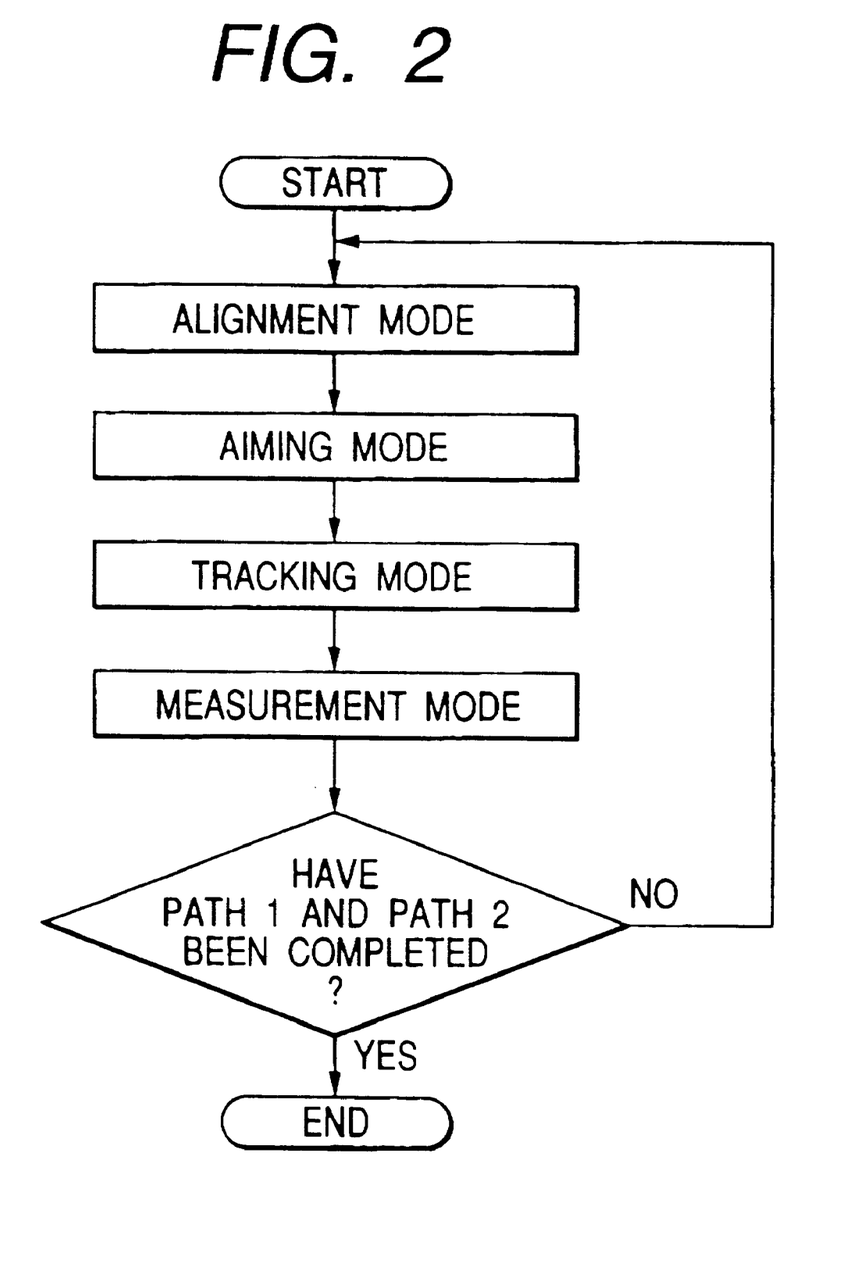
FIG. 2 is a diagram to show an overall flowchart.

FIG. 2 is a diagram to show the flowchart of the metering method. The sequential metering operation is composed of four modes, which are an alignment mode, an aiming mode, a tracking mode, and a measurement mode. For obtaining the velocity of blood flow at a certain point on the fundus, it is necessary to check the sign inversion of the beat signal and the sequential metering operation including the alignment mode has to be carried out repeatedly twice with switching of incident light paths in order to implement the check of the sign inversion. The measurement through the first incident light path is carried out in path 1 and the measurement through the second incident light path in path 2. The switching of optical paths is carried out by the switching mirror 34 in FIG. 7.

Figure 3:
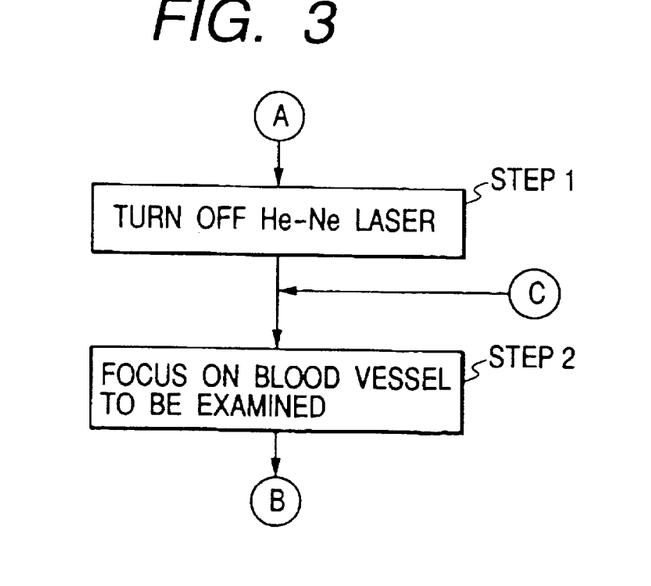
FIG. 3 is a diagram to show a flowchart of an alignment mode.

FIG. 3 is the flowchart of the alignment mode, in which the power is first supplied to the personal computer 122 and to the main-body measurement head 125 to make necessary programs active and in that state the patient puts his or her jaw on the jaw support 124. The operation is carried out under control of the personal computer 22. In step 1 the He—Ne laser light source (laser diode 36) is turned off. In step 2, while the eye is guided so as to locate the blood vessel to be measured on the fundus as close to the center as possible by manipulating the control rod 126, the internal fixation light control knob 130, and the focus knob 131, the stage movable portion 123 is actuated to make the fundus of the eye to be examined in focus. Then, the computer moves into the aiming mode illustrated in FIG. 4.

Figure 4:
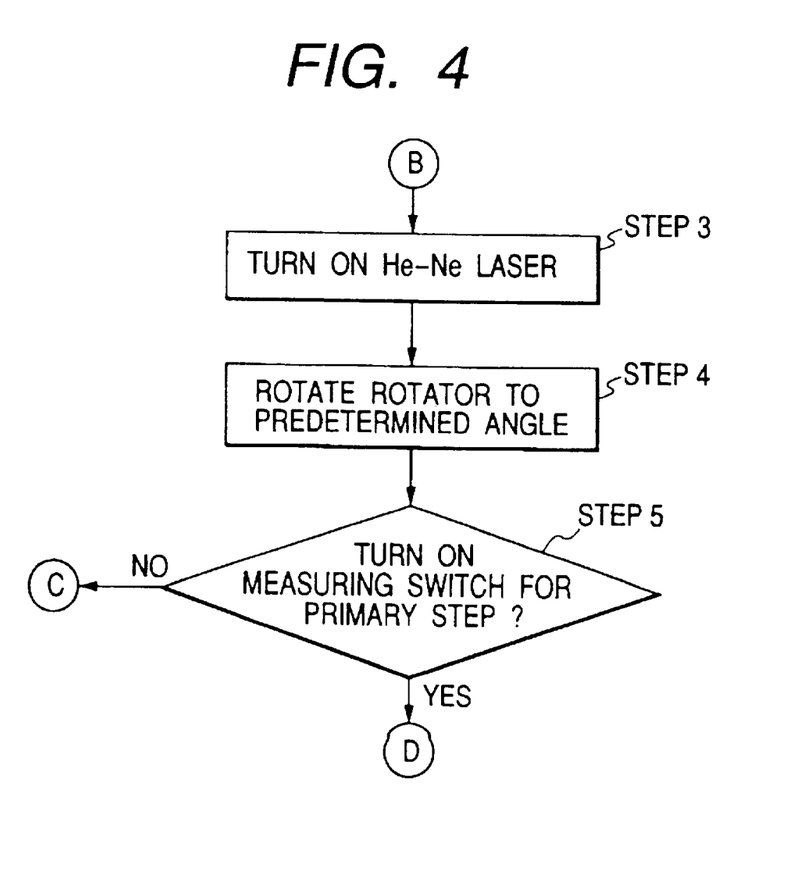
FIG. 4 is a diagram to show a flowchart of an aiming mode.

FIG. 4 is the flowchart of the aiming mode. In step 3 the He-Ne laser light source is turned on to guide the illumination He—Ne laser light for tracking and capturing the blood-vessel diameter and eye movement, to the eye to be examined. In step 4 the image rotator is rotated so as to make the angle of $\beta$ of FIG. 10 in the prior art example equal to 0° with respect to the blood vessel to be measured from the beam shape. If the image is out of focus in step 5, the computer will return to step 2 of FIG. 3. If the image is in focus, the examiner will depress a primary step of the measuring switch 127 provided at the control rod 126, thereby transferring to the tracking mode illustrated in FIG. 5.

Figure 5:
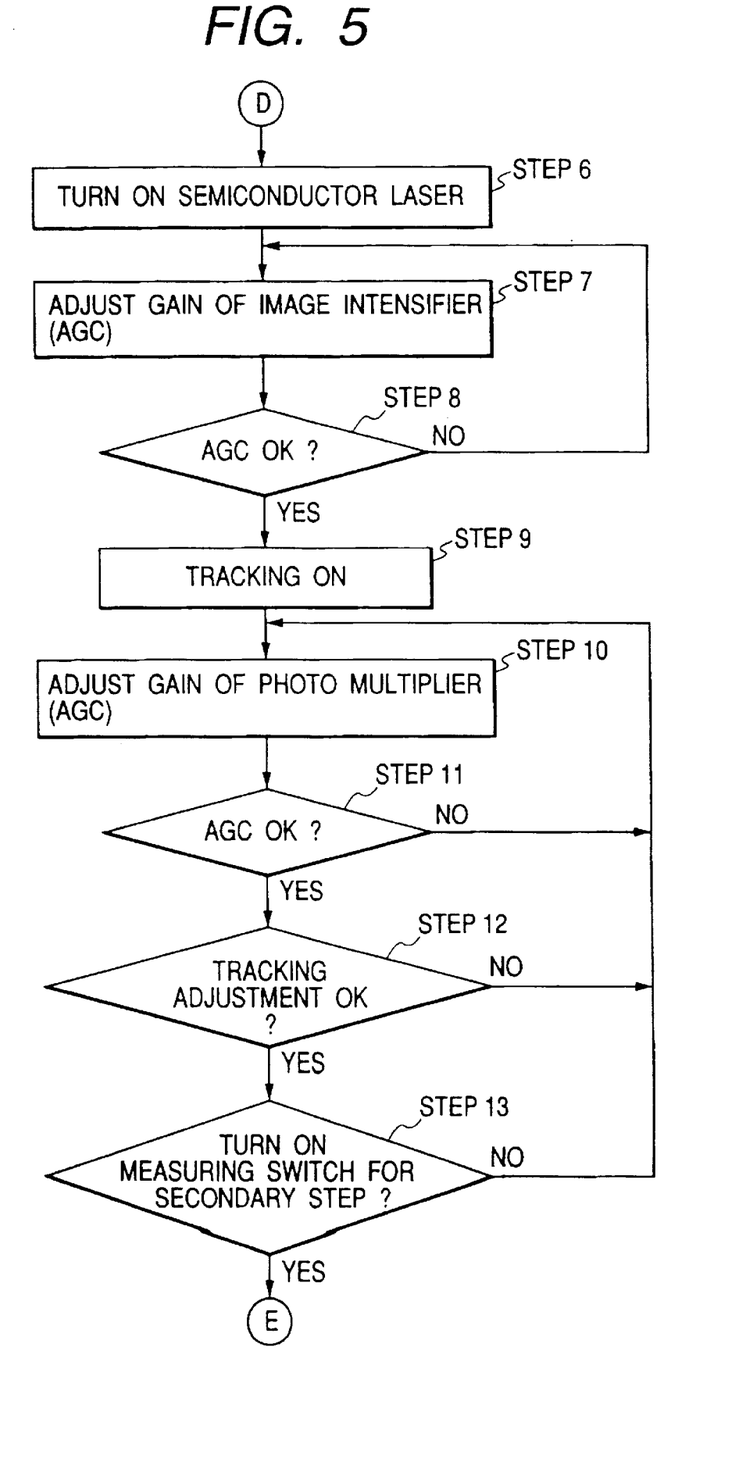
FIG. 5 is a diagram to show a flowchart of a tracking mode.

FIG. 5 is the flowchart of the tracking mode. In step 6 the semiconductor laser-light source to emit the measuring beam for gaining the blood-flow velocity is turned on to emit weak light at a low level. The measuring beam travels through the first incident light path to the measured blood vessel, and the tracking is activated. In step 7, in order to optimize the amplitude of the video signal of the blood-vessel image by the illumination He—Ne laser light, the amplitude of the video signal is read and the gain of the image intensifier (CCD 42) is automatically controlled. In step 8, if the control is insufficient, the computer will return to step 7. On the other hand, when the optimization of the blood-vessel image is completed, the computer goes to step 9 to turn the tracking switch on to gain the blood-vessel position from the video signal. In step 10, the amplitude of the Doppler signal including the eye movement is read and the gains of the two photomultipliers (46a, 46b) are controlled to an optimum value. In step 11, if the control of the gains is insufficient, the computer will return to step 10.

When it is determined in step 11 that the control is completed, and when the position of the beam spot of the semiconductor-laser-light source deviates from the blood vessel to be measured because of the aberration of the patient's eye in step 12, the tracking adjustment dial 128 is turned and controlled so as to irradiate the blood vessel correctly, and the gain control of the photomultipliers is carried out again. On the other hand, once the gains of the photomultipliers and the tracking adjustment are controlled, each to a predetermined value, the examiner depresses a secondary step of the measuring switch 127 in step 13 to go into the measurement mode illustrated in FIG. 6. On the other hand, if the tracking adjustment is not sufficient yet, the computer will return to step 10.

Figure 6:
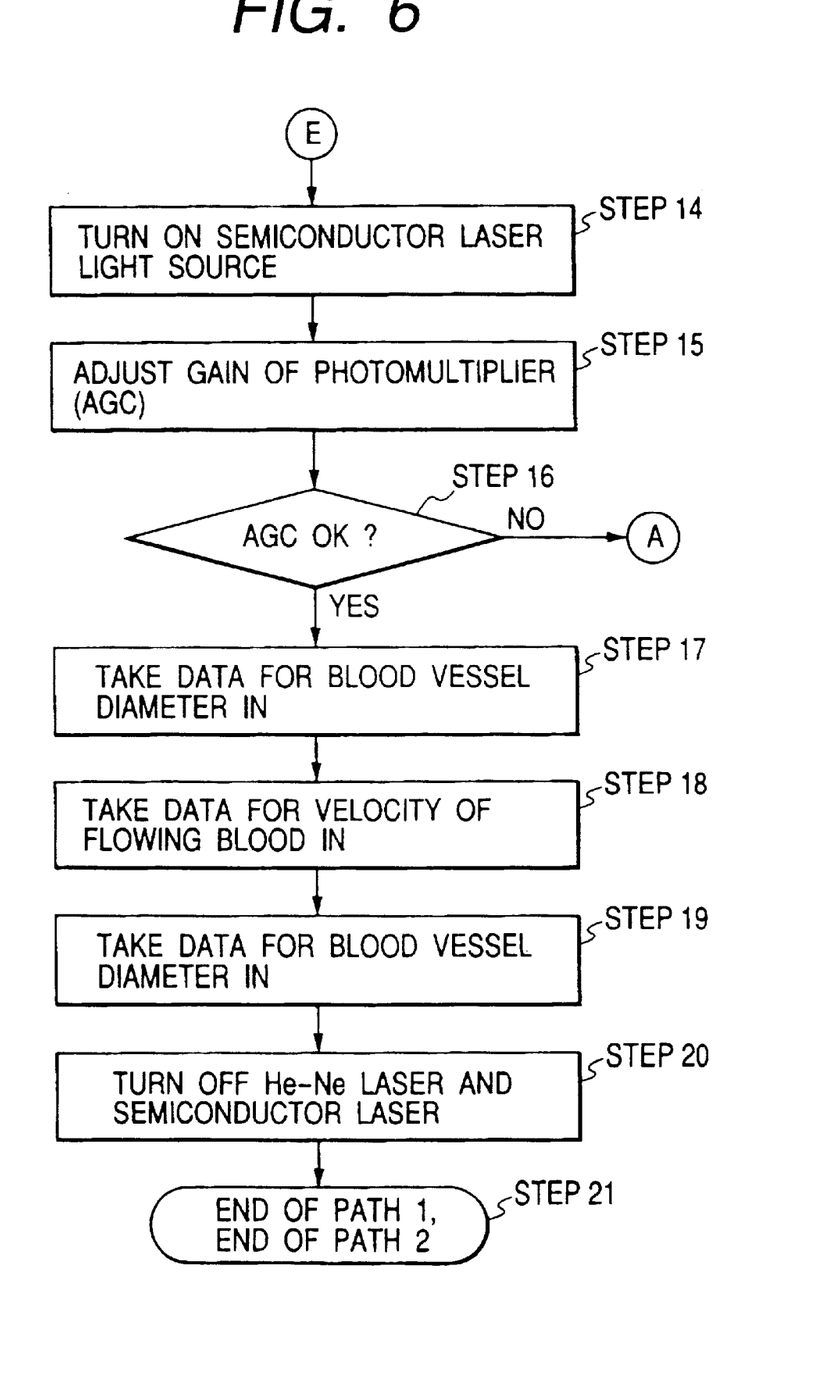
FIG. 6 is a diagram to show a flowchart of a measurement mode.

FIG. 6 is the flowchart of the measurement mode. In step 14 the semiconductor-laser-light source is changed first into the power of the high level and in step 15 the gains of the photomultipliers are again controlled against the high power. If step 16 results in failing to readjust the gains well, the illumination He-Ne laser light will be turned off and the computer will move into the alignment mode of FIG. 3. On the other hand, when the readjustment of the gains is effected well, steps 17, 18, and 19 are carried out to take the measuring light into the two photomultipliers and successively compute data of the blood-vessel diameter, the blood-vessel velocity, and again the blood-vessel diameter. In step 20, the illumination He—Ne laser light source and the semiconductor-laser-light source are turned off simultaneously and in step 21 the first measurement in path 1 is completed.

Next, the measuring light from the semiconductor-laser-light source passes through the second incident light path to reach the measured blood vessel and the second measurement in the second path is carried out in the alignment mode, in the aiming mode, in the tracking mode, and in the measurement mode, as in the first measurement, thereby computing the blood-flow velocity of the same blood vessel. By once terminating the measurement in each of the paths 1, 2 in this way, the restraint time and the laser-light irradiation time during the measurement to the patient can be reduced and the accurate tracking can be carried out even if the measurement time is not less than one pulsation. The issue of the sign of the Doppler beat signal obtained can be solved by the measurement from the two directions.

Since the fundus-blood-blow metering apparatus according to the present invention is arranged to measure the first blood-flow velocity as to a measurement point at one position, again carry out the alignment of the positional relation with the eye to be examined, and then measure the second blood-flow velocity at a different angle of incidence as described above, the correct blood-flow velocity can be computed.

What is claimed is:

1. A method for measuring the blood flow of a fundus blood vessel on an eye to be examined, by irradiating the blood vessel with a light beam, detecting scattered and reflected light from the irradiated vessel, and calculating the velocity of the blood flow based on the detection, said method comprising the steps of:

executing a first measurement of the blood flow while irradiating the blood vessel with a light beam from a first direction;

carrying out alignment related to the eye after executing the first measurement in said first measurement executing step;

allowing an operator to confirm the alignment state and awaiting the operator's order; and executing a second measurement of the blood flow, based on the operator's order, while irradiating the blood vessel with a light beam from a second direction different from the first direction.

2. The method according to claim 1, further comprising the step of automatically adjusting a gain of the detection during the first and second measurements.

3. The method according to claim 1, wherein said alignment related to the eye comprises focus adjustment.

4. The method according to claim 1, wherein said alignment related to the eye comprises tracking adjustment.

5. The method according to claim 1, wherein said detection is executed by detecting the scattered and reflected light with a plurality of detectors arranged at different angles.

6. An apparatus for measuring a fundus blood vessel on an eye to be examined comprising:

an irradiation system having a light source, for irradiating the blood vessel with a light beam;

a detection system having detectors for detecting scattered and reflected light from the irradiated vessel;

an operation device allowing an operator to order measurement; and a controller configured to:

execute a first measurement of the blood flow while controlling said irradiation system to irradiate the blood vessel with a light beam from a first direction;

carry out alignment related to the eye after the first measurement;

await an operator's order with said operation device; and execute a second measurement of the blood flow, based on the operator's order with said operation device, while controlling said irradiation system to irradiate the blood vessel with a light beam from a second direction different from the first direction.

7. The apparatus according to claim 6, further comprising an automatic gain controller configured to automatically adjust the gain of the detectors during the first and second measurements.

8. The apparatus according to claim 6, further comprising a focus adjustment system for performing a focus operation to carry out the alignment controlled by said controller.

9. The apparatus according to claim 6, further comprising a tracking system configured to perform a tracking operation.

10. The apparatus according to claim 9, wherein said tracking system comprises an image intensifier and an automatic gain controller for the image intensifier.

11. The apparatus according to claim 6, wherein the first measurement is commenced based on the operator's order with said operation device.

* * * * *

UNITED STATES PATENT AND TRADEMARK OFFICE
CERTIFICATE OF CORRECTION

PATENT NO. : 6,302,850 B1
DATED : October 16, 2001
INVENTOR(S) : Mamoru Tsukada

It is certified that error appears in the above-identified patent and that said Letters Patent is hereby corrected as shown below:

Column 2,
Line 4, "a" should read -- α --.
Line 17, "P" should read -- β --.

Column 4,
Line 33, "the" should read -- has --.

Column 6,
Line 4, "focoused" should read -- focused --; and "I" should read -- image I --.

Column 8,
Line 51, "=0°" should read -- β=0° --.

Signed and Sealed this

Seventh Day of May, 2002

Attest:

Attesting Officer

JAMES E. ROGAN
Director of the United States Patent and Trademark Office